United States Patent [19]
Lelli et al.

[11] Patent Number: 5,363,863
[45] Date of Patent: Nov. 15, 1994

[54] LUMBAR SUPPORT BELT

[76] Inventors: Charles Lelli, 45, rue Rébeval, 75019 Paris; Marc L. Lelli, 7, rue Tardieu, 75018 Paris, both of France

[21] Appl. No.: 51,225

[22] Filed: Apr. 23, 1993

[51] Int. Cl.$^5$ .......................... A61F 5/37; A61F 5/00
[52] U.S. Cl. ..................................... 128/876; 602/19
[58] Field of Search .................. 128/869, 876; 602/5, 602/19; 2/2, 337, 338

[56] References Cited

U.S. PATENT DOCUMENTS

| | | | |
|---|---|---|---|
| 1,940,904 | 12/1933 | Dayton | 602/19 |
| 2,181,689 | 11/1939 | Bell | 602/19 |
| 2,552,475 | 5/1951 | Austlid | 602/19 |
| 2,760,486 | 8/1956 | Ward | 602/19 |
| 2,778,358 | 1/1957 | Keles | 602/19 |
| 2,808,050 | 10/1957 | Ward | 602/19 |
| 2,813,526 | 11/1957 | Beebe | 602/19 |
| 3,095,875 | 7/1963 | Davidson | 602/19 |
| 3,097,640 | 7/1963 | Morgan | 602/19 |
| 3,351,053 | 11/1967 | Stuttle | 602/19 |

FOREIGN PATENT DOCUMENTS

| | | |
|---|---|---|
| 0027602 | 10/1980 | European Pat. Off. |
| 1104562 | 11/1955 | France |
| 1390831 | 1/1965 | France |
| 2023334 | 8/1970 | France |
| 2589723 | 5/1987 | France |
| 740507 | 11/1955 | United Kingdom |

Primary Examiner—Michael A. Brown
Attorney, Agent, or Firm—Finnegan, Henderson, Farabow, Garrett & Dunner

[57] ABSTRACT

A lumbar support belt includes a rear lumbar support piece (1), a front abdominal support piece (2) constituted by two independent portions (2a, 2b), two lateral hip support pieces (3), length adjustment means (4, 5) connecting the lateral pieces (3) to the rear piece (1) and to the two portions (2a, 2b) of the front piece (2), and closure means (6) suitable for connecting these two portions.

12 Claims, 3 Drawing Sheets

LUMBAR SUPPORT BELT

BACKGROUND OF THE INVENTION

The present invention relates to a lumbar support belt.

Lumbar support belts presently in use are generally formed by a single elastic strap comprising metallic strips in its median portion and closure systems in the vicinity of its free ends.

These belts do not, however, always give complete satisfaction. Indeed, they provide unsatisfactory lumbar support, with the metallic strips exerting on the user's spinal column a pressure that varies according to his or her posture and movements. Furthermore, they do not provide efficient, balanced abdominal support. Moverover, as their end portions are rigid in one case and elastic in the other, they tend to turn around the user's body, which is inconvenient for the latter.

SUMMARY OF THE INVENTION

The present invention proposes, more particularly, to remedy these drawbacks and, to do so, it provides for a lumbar support belt which is characterized in that it includes a rear lumbar support piece, a front abdominal support piece constituted by two independent portions, two independent lateral hip support pieces, length adjustment means connecting the lateral pieces to the rear piece and to the two portions of the front piece, and closure means suitable for connecting these two portions.

When this belt is in place, its rear piece remains constantly pressed against the user's spinal column and ensures efficient lumbar support, whatever the latter's posture and movements.

Its front piece, for its part, suitably supports the user's abdominal region, which is not the case with presently used belts.

Furthermore, the length adjustment means enable the belt to be fitted easily around the user's waist in such a way that the latter's movements are not impeded.

The belt according to the invention has the further particularity of not turning around the user's waist when the latter moves about or performs various movements.

Advantageously, the rear lumbar support piece includes a metallic reinforcement comprising a main frame designed to be placed along the user's spinal column, and two secondary frames, fixed to the main frame, perpendicularly thereto, as well as a protective envelope enclosing the metallic reinforcement.

Thanks to the special structure of its rear portion, the belt according to the invention firmly supports the lumbar region of the user, who can thus exercise risk-entailing sporting or professional activities in complete safety.

Preferably, the face of the longitudinal sides of the main frame that is designed to be directed towards the spinal column is convex, whereas the corresponding face of the longitudinal sides of the secondary frames has three concave sections, separated by the longitudinal sides of the main frame.

The special form of the frames constituting the metallic reinforcement allows the rear portion of the belt to be elastically deformed so as to adapt constantly to the user's morphology. It should be noted, moreover, that the central concave sections prevent the reinforcement from coming into contact with the posterior vertebral spines of the user.

To facilitate the pressing of the rear piece of the belt against the user's lumbar region, it is desirable for the protective envelope to be made of a synthetic material and to have two lateral cut away portions in the region of those parts of it located betwen the secondary frames, outside the main frame.

Furthermore, to ensure that the belt cannot transmit to the user any vibrations that may be applied to it, the protective envelope includes an inner panel of low density foam integral with an outer panel of high density foam provided with a protective covering, the inner panel being designed to be turned towards the spinal column.

According to one particular form of embodiment, the length adjustment means include straps fixed to each of the lateral pieces and passing through rings provided respectively on the rear piece and on the portions constituting the front piece, complementary fixing members provided respectively on the lateral pieces and on the straps being designed to be engaged selectively in order to fix the free ends of the latter to the said lateral portions in different positions.

It thus suffices to engage special complementary fixing members in order to adjust the length of the belt and adjust the tension of the latter optimally as a function of the user's waist.

The complementary fixing members provided on the lateral pieces and on the straps passing through the rings in the rear piece can be press-studs.

As to the complementary fixing members provided on the lateral pieces and on the straps passing through the rings in the portions constituting the front piece, these can be self-gripping strips.

To enhance the user's comfort, it is preferable for the lateral pieces to be made of an elastic material.

If the user wishes to limit the elastic elongation of the lateral pieces, for example to increase the mechanical efficiency of the rear piece, it is desirable for the straps passing through the rings of the portions constituting the front piece to extend over the straps passing through the rings of the rear piece, self-gripping strips being fixed onto the opposite faces of the straps in order to interconnect the latter.

So that the user can perform his or her activities under optimum conditions, it is preferable, moreover, for the front piece to be smaller than the rear piece, and for its component parts to comprise at least one inner layer of low density foam integral with an outer layer of high density foam provided with a protective covering, the inner layer being designed to be turned towards the subject's abdomen.

Furthermore, to ensure that the belt cannot become unfastened at an untimely moment, when the user is exercising his or her habitual activities, it is desirable for it to include two closure means, each constituted by a male piece and an female piece, the male pieces being fixed to one of the portions constituting the front piece, while the female pieces are fixed to the other portion.

BRIEF DESCRIPTION OF THE DRAWINGS

One form of embodiment of the present invention will now be described by way of a non-limitative example, with reference to the annexed drawings, wherein.

DETAILED DESCRIPTION OF THE INVENTION

Figure 1:
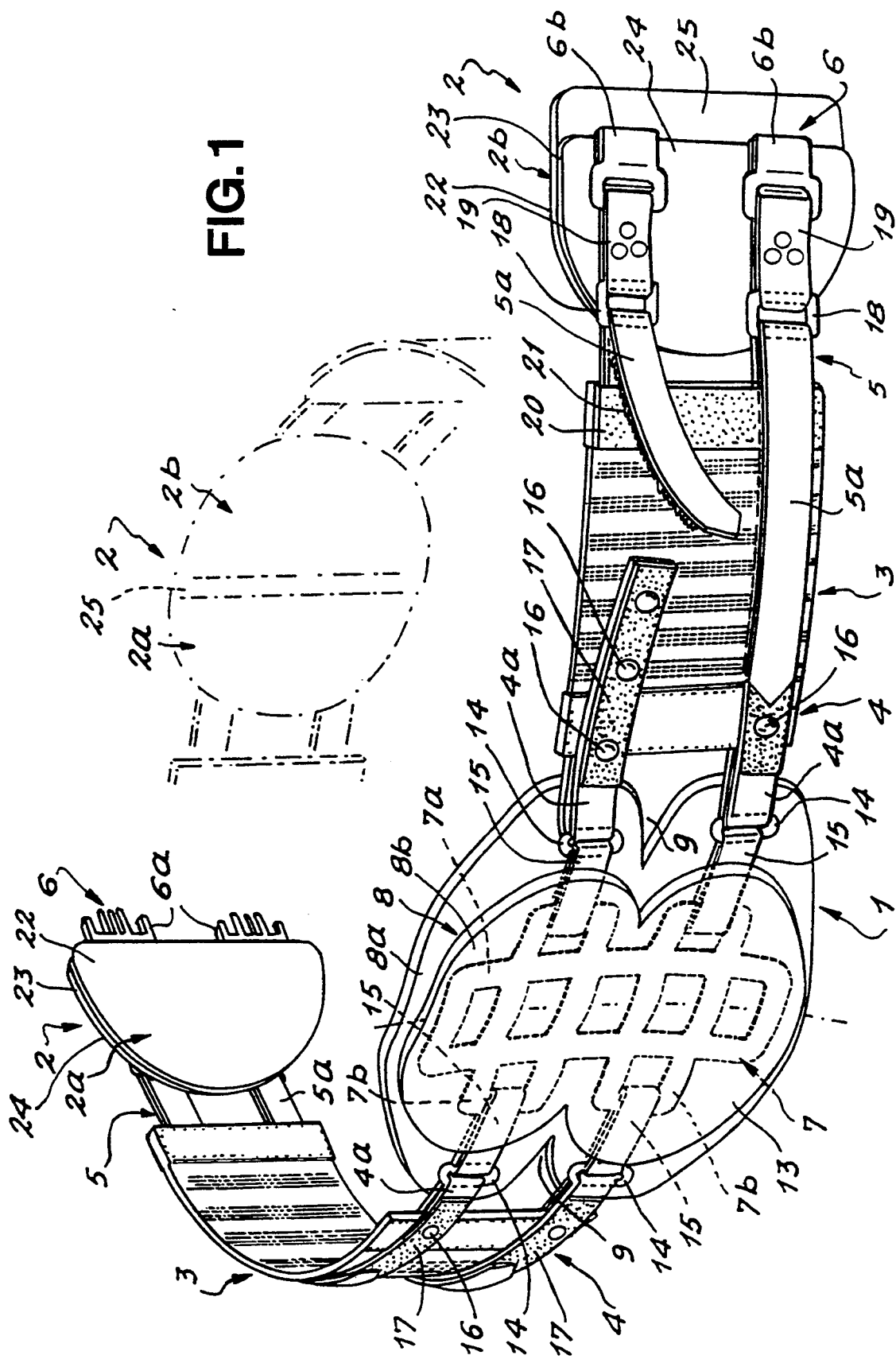
FIG. 1 is a schematic perspective view of a belt according to the invention, the outer face of the belt being turned outwards
Figure 2:
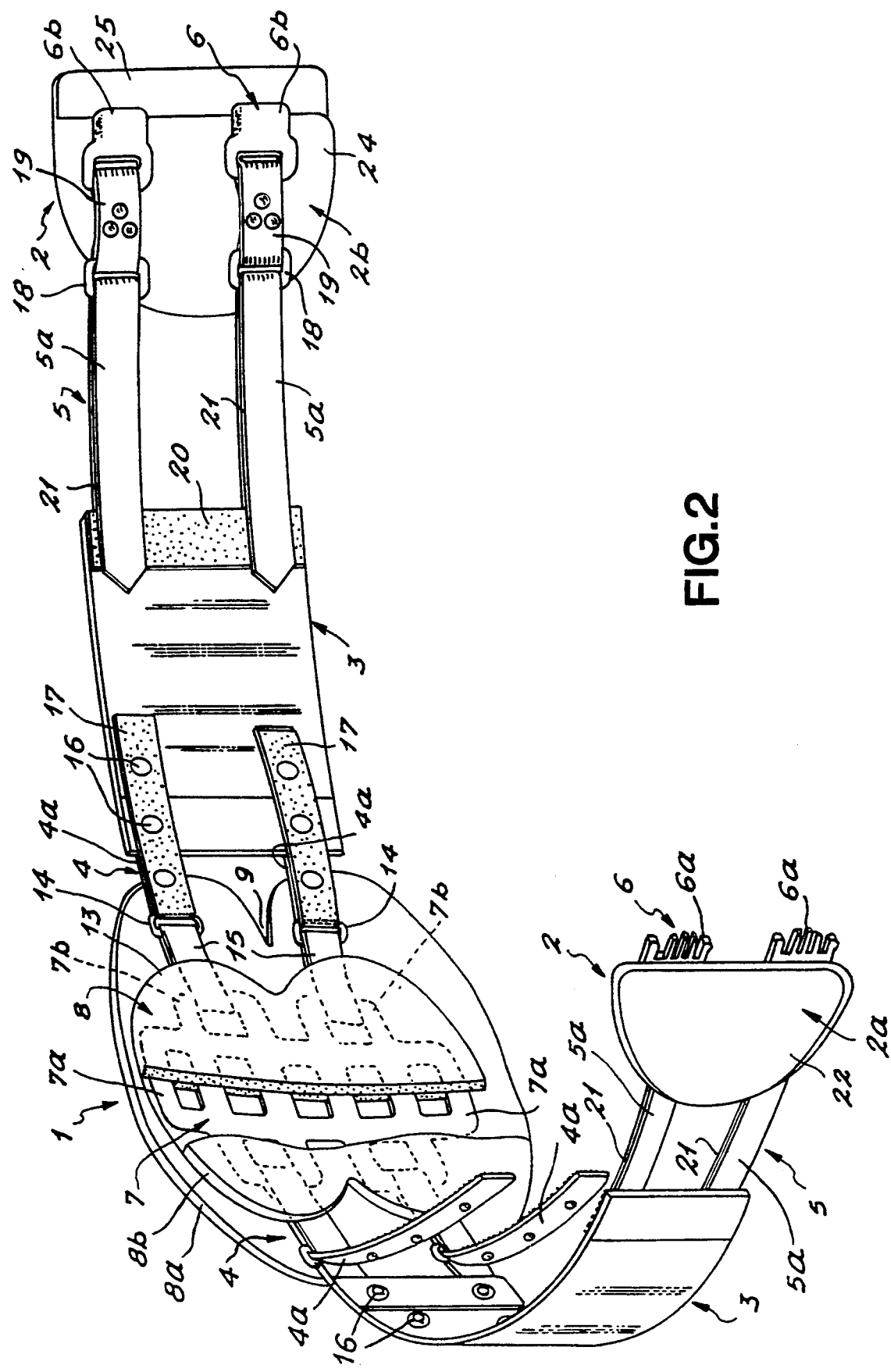
FIG. 2 is another schematic perspective view of the belt, shown in FIG. 1, its outer face being turned inwards.

The lumbar support belt shown in FIGS. 1 and 2 includes a rear piece 1, a front piece 2 constituted by two independent portions, 2a, 2b (represented in dot and dash lines in FIG. 1, connected to one another), two lateral pieces 3, rear adjustment means 4 connecting the lateral pieces 3 to the rear piece 1, front adjustment means 5 connecting, for their part, lateral pieces 3 to portions 2a, 2b of front piece 2, and two closure means 6 designed to connect portions 2a, 2b to one another and to close the belt.

Rear piece 1 includes a metallic reinforcement 7 comprising a main frame 7a designed to be placed along the user's spinal column, and two secondary frames 7b, fixed to main frame 7a, perpendicularly thereto, as well as a protective envelope 8 enclosing reinforcement 7.

The face of the longitudinal sides of main frame 7a that is located on the inner face side of the belt is convex, whereas the corresponding face of the longitudinal sides of secondary frames 7b has three concave sections separated by the longitudinal sides of the main frame.

Metallic reinforcement 7 is elastically deformable and, thanks to the special configuration of the frames that constitute it, it allows rear portion 1 of the belt to remain in permanent contact with the user's lumbar region, whatever the latter's movements.

Protective envelope 8 has two lateral cut away portions 9 in the region of its portions located between secondary frames 7b, outside main frame 7a, these cut away portions making it easier to adapt rear piece 1 to the user's morphology.

Envelope 8, which is made of synthetic material to make the belt especially comfortable, includes an inner panel 8a, located on the inner face side of the belt, and an outer panel 8b, located on the opposite side, these panels being fixed against one another and clasping metallic reinforcement 7 between them.

Figure 3:
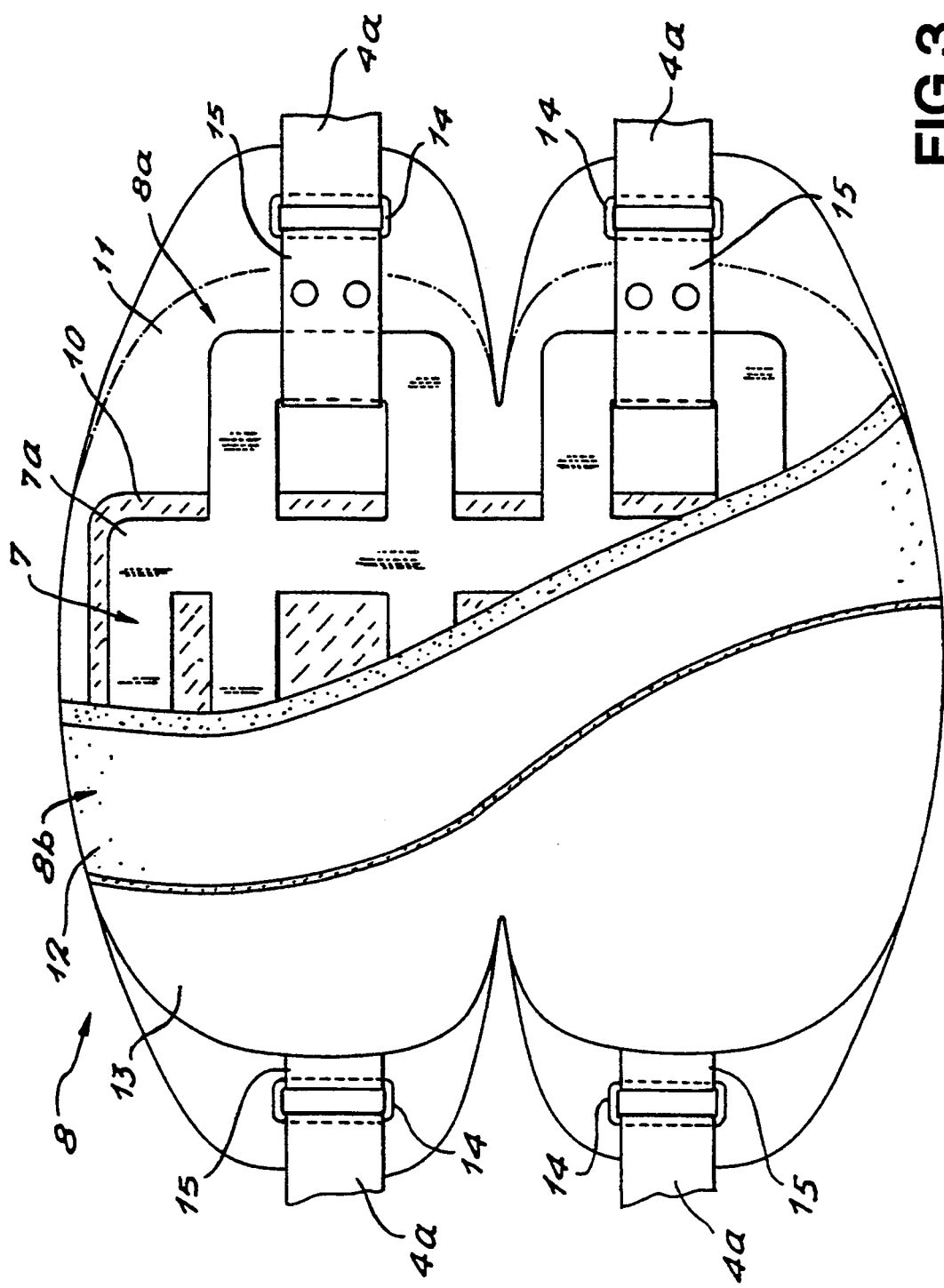
FIG. 3 is a plan view, with certain parts cut away, of the rear piece of the belt.

In the form of embodiment, given by way of example, contemplated here, inner panel 8a is larger than outer panel 8b. As shown in FIG. 3, it includes a first platelet of low density foam 10, fixed against main frame 7a and having dimensions slightly greater than those of the latter, and a second platelet of low density foam 11, fixed to platelet 10, platelet 11 having dimensions greater than those of metallic reinforcement 7.

As to outer panel 8b, it includes a first platelet of high density foam 12 fixed against the metallic reinforcement and having dimensions greater than those of the latter, and a protective covering platelet 13 made, for example of an imitation leather material, covering platelet 11.

It should be noted here that the different platelets constituting envelope 8 are adhered to one another and made, preferably, of polyethylene foam, the high density foam platelet providing outer protection in the event of impact, and permitting the filtering of vibrations, while the two low density foam platelets are designed to protect the spinal column directly, to filter vibrations, to prevent the user from catching chills and to ensure user comfort.

Of course, envelope 8 could have a structure other than that which has just been described, without thereby departing from the scope of the present invention.

Rear adjusting means 4 include four straps 4a, fixed two by two to lateral pieces 3, these straps projecting on the transverse sides of lateral pieces 3 that are turned towards rear piece 1 and passing through rings 14 borne by fasteners 15 fixed to the transverse sides of secondary frames 7b of the reinforcement 7. Press-studs 16, the mating members of which are fixed, the ones on the outer face of lateral pieces 3 and the others on the face of straps 4a that is designed to be fastened down onto the said lateral pieces, allow the distance between the latter and the rear piece 1 to be adjusted. It suffices, in fact, to engage selectively particular press-studs 16 in order to effect this adjustment.

It should be noted here that straps 4a are preferably made of a synthetic textile material, for example polypropylene fibres. They could, however, be made of any other flexible material.

It should also be noted that their face that is turned outwards after they have been fastened down against lateral pieces 3 bears, in the vicinity of their free end, a self-gripping strip 17, the function of which will be described later.

Front adjusting means 5 include four straps 5a fixed two by two to lateral pieces 3, these straps projecting on the sides of lateral pieces 3 that are turned towards portions 2a, 2b of front piece 2 and passing through rings 18 borne by fasteners 19 fixed to the outer face of portions 2a, 2b.

Lateral pieces 3 are provided, along their transverse side that is turned towards portions 2a, 2b, with a self-gripping strip 20. Similarly, straps 5a are provided, on their face designed to be fastened down onto lateral pieces 3, with a self-gripping strip 21.

It will easily be appreciated that, by pressing particular areas of strips 21 of straps 5a against strips 20 of lateral pieces 3, the distance between the latter and portions 2a, 2b of front piece 2 can be adjusted with relative precision.

It is pointed out here that straps 5a, like straps 4a, are preferably made of a synthetic textile material, for example polypropylene.

With more particular reference to FIG. 1, it will be noted that it may be desirable for front straps 5a to be sufficiently long for it to be possible for their self-gripping strip 21 to be pressed against self-gripping strip 17 of rear straps 4a. Indeed, as lateral pieces 3 are preferably made of elastic material, the engagement of self-gripping strips 17 and 21 can substantially limit the extension capability of lateral pieces 3, which may be the aim of the user when the latter has to perform or to make considerable efforts.

On the other hand, if the user wishes to benefit from the advantages procured by the elasticity of lateral pieces 3, he or she will have to attach straps 5a less tightly.

Front piece 2 is smaller than rear piece 1. In the form of embodiment contemplated here, its component parts, 2a, 2b are constituted by superposing a platelet of low density foam 22, located on the inner face side of the belt, a high density foam platelet 23 and a protective covering platelet 24, of imitation leather, for example, located on the outer face side of the belt.

The platelets constituting portions 2a, 2b of front piece 2 are adhered to one another and preferably made of polyethylene foam. Nothing prevents them, however, from being made of an other material, or from their being other than 3 in number.

It is to be noted here that piece 2b bears, on its face located on the inner side of the belt, a tab 25 designed to take up a position beneath piece 2a when the belt is closed, as represented in dot and dash lines in FIG. 1.

Fasteners 19 are fixed to portions 2a, 2b of front piece 2 by rivets and they bear the two closure means 6 at their end opposite that bearing a buckle 18.

In a manner known per se, closure means 6 are each constituted by a male piece 6a, fixed to portion 2a, and by a female piece 6b, fixed to portion 2b. It thus suffices to introduce male pieces 6a into female pieces 6b to close the belt, and to act on a locking catch (not represented) provided on the male pieces 6a to separated the latter from female pieces 6b and open the belt.

To install the belt according to the invention around his or her body, the user can proceed as follows:

place the belt flat in front of him or her in such a way that the outer face thereof is turned towards him or her;

adjust the distance between the rear piece 1 and the lateral pieces 3 by engaging certain press-studs 16, the complementary members of which are respectively provided on straps 4a and on lateral pieces 3;

unfasten the self-gripping strips 21 provided on straps 5a;

don the belt by taking hold of portions 2a, 2b of front piece 2, making sure that rear piece 1 is located correctly opposite the spinal column;

engage male pieces 6a and female pieces 6b of closure means 6;

adjust the distance between lateral pieces 3 and portions 2a, 2b of front piece 2 by pressing against self-gripping strips 20 of lateral pieces 3 the appropriate portions of self-gripping strips 21 of straps 5a. To facilitate matters, it is preferable for the user to make the adjustment starting with the lower straps 5a; and fix the free ends of straps 5a, if applicable, to self-gripping strips 17 on rear straps 4a.

To remove the belt, of course, the user merely has to separate the male and female pieces of the closure means.

We claim:

1. A lumbar support belt comprising a rear lumbar support piece, a front abdominal support piece made up of two independent portions having closure means for connecting said portions together, two independent lateral hip support pieces, one lateral support piece being located between a first side of the rear support piece and one of the two portions of the front support piece and the other lateral support piece being located between the opposite side of the rear support piece and the other of the two portions of the front support piece, length adjustment means connecting each lateral support piece to the rear support piece and separate length adjustment means connecting each lateral support piece to one of the portions of the front support piece.

2. The lumbar support belt of claim 1, wherein the rear lumbar support piece comprises a metallic reinforcement having a main frame adapted to be placed along the spinal column of the user and two secondary frames, fixed to the main frame perpendicular thereto, and a protective envelope enclosing the metallic reinforcement.

3. The lumbar support belt of claim 2, wherein the face of the longitudinal sides of the main frame that is to be turned towards the spinal column is convex, and the corresponding face of the longitudinal sides of the secondary frames has three concave sections separated by the longitudinal sides of the main frame.

4. The lumbar support belt of claim 2, wherein the protective envelope is made of a synthetic material and has two lateral cut away portions located between the secondary frames and outside the main frame.

5. The lumbar support belt of claim 4, wherein the protective envelope includes an inner panel made of low density foam integral with an outer panel made of high density foam provided with a protective covering, the inner panel being adapted to face the user's spinal column.

6. The lumbar support belt of claim 1, wherein both of the length adjustment means comprises straps fixed to the lateral support pieces that pass through cooperating rings on the rear piece and on the portions of the front support piece and complimentary fixing means on the lateral support pieces and on the straps that permit the straps to be selectively fixed to said lateral support pieces in different positions.

7. The lumbar support belt of claim 6, wherein the complimentary fixing means on the lateral support pieces and on the straps that pass through the rings on the rear support piece are press-studs.

8. The lumbar support belt of claim 7, wherein the complimentary fixing means on the lateral support pieces and on the straps that pass through the rings on the portions of the front support piece are self-gripping strips.

9. The lumbar support belt of claim 6, wherein the straps that pass through the rings of the portions of the front support piece extend over the straps that pass through the rings of the rear support piece, self-gripping strips being fixed on the opposite faces of the straps to connect them together.

10. The lumbar support belt of claim 1, wherein the lateral support pieces are made of an elastic material.

11. The lumbar support belt of claim 1, wherein the two portions of the front support piece each include an inner layer of low density foam integral with an outer layer of high density foam provided with a protective covering, the inner layer being adapted to face the user's abdomen.

12. The lumbar support belt of claim 1, wherein the closure means comprises male pieces and female pieces, the male pieces being fixed to one of the two portions of the front support piece and the female pieces being fixed to the other portion.

* * * * *